United States Patent [19]

Madras

[11] Patent Number: 5,390,544

[45] Date of Patent: Feb. 21, 1995

[54] METHOD AND APPARATUS FOR NON-DESTRUCTIVE EVALUATION OF COMPOSITE MATERIALS WITH CLOTH SURFACE IMPRESSIONS

[75] Inventor: Eric I. Madras, Yorktown, Va.

[73] Assignee: The United States of America as represented by the Administrator of the National Aeronautics and Space Administration, Washington, D.C.

[21] Appl. No.: 110,278

[22] Filed: Jul. 16, 1993

[51] Int. Cl.⁶ .............................................. G01N 9/24
[52] U.S. Cl. ..................................................... 73/602
[58] Field of Search .................. 73/602, 599, 600, 620

[56] References Cited

U.S. PATENT DOCUMENTS

| 4,470,303 | 9/1984 | O'Donnell | 73/602 |
| 4,545,250 | 10/1985 | Miwa | 73/602 |
| 4,862,892 | 9/1989 | Green | 73/620 |
| 4,866,614 | 9/1989 | Tam | 364/413.25 |

OTHER PUBLICATIONS

*Characterization of Porosity in Continuous Fiber-Reinforced Composites With Ultrasonic Backscattering*, Ronald A. Roberts, Materials and components Technology Division, Argonne National Laboratory, Argonne, Ill. 60439, Review of Progress in Quantitative Nondestructive Evaluation, vol. 78, pp. 1153–1162 (1988).

*Quantitative Non-Destructive Evaluation of Composite Materials Based on Ultrasonic Wave Propagation*, Semi-annual Progress Report, Sep. 15, 1986–Mar. 15, 1987, Dr. James G. Miller, Principal Investigator, Professor of Physics, Washington University, Department of Physics, Laboratory for Ultrasonics, St. Louis, Mo. 63130.

*Measured Effects of Surface Cloth Impressions on Polar Backscatter and Comparison with a Reflection Grating Model*, E. I. Madaras, NASA, Langley Research Center, Hampton, Va. 23665; Edwin F. Brush, III, Dept. of Physics, Colorado College, Colorado Springs, Colo. 80903; S. Lori Bridal, Mark R. Holland, J. G. Miller, Laboratory for Ultrasonics, Dept. of Physics, Washington University, St. Louis, Mo. 63130; 19th Annual Review of Progress in Quantitative Nondestructive Evaluation, La Jolla, Calif., Jul. 20–24, 1992.

*Quantitative Non-Destructive Evaluation of Composite Materials Based on Ultrasonic Wave Propagation*, Semi-annual Progress Report, Mar. 15, 1985–Sep. 15, 1985, Dr. James G. Miller, Principal Investigator, Professor of Physics, Washington University, Department of Physics, Laboratory for Ultrasonics, St. Louis, Mo. 63130.

*Physical Principles of Ultrasonic Non-Destructive Evaluation of Advanced Composites*, Semi-annual Progress Report, Mar. 15–Sep. 14, 1988, Dr. James G. Miller, Principal Investigator, Professor of Physics, Washington University, Dept. of Physics, Laboratory for Ultrasonics, St. Louis, Mo. 63130.

*Characterization of Porosity in Graphite/Epoxy Composite Laminates With Polar Backscatter and Frequency Dependent Attenuation*, IEEE 1987, Ultrasonics Symposium, pp. 827–830, S. M. Handley, M. S. Hughes, J. G. Miller, Physics Dept., Washington University, St. Louis, Mo. 63130, E. I. Madaras, NASA Langley Research Center, Hampton, Va. 23665.

(List continued on next page.)

Primary Examiner—Hezron E. Williams
Assistant Examiner—Christine K. Oda
Attorney, Agent, or Firm—Linda B. B. Blackburn

[57] ABSTRACT

A method and related apparatus for non-destructive evaluation of composite materials by determination of the quantity known as Integrated Polar Backscatter, which avoids errors caused by surface texture left by cloth impressions by identifying frequency ranges associated with peaks in a power spectrum for the backscattered signal, and removing such frequency ranges from the calculation of Integrated Polar Backscatter for all scan sites on the composite material.

7 Claims, 5 Drawing Sheets

OTHER PUBLICATIONS

*Variations in Ultrasonic Backscatter Attributed to Porosity*, Review in Progress in Quantitative NDE v. 8B, pp. 1275–1284, D. E. Yuhas, C. L. Vorres, and Ron Roberts, Magnaflux Advanced Research, 2301 Arthur Avenue, Elk Grove Village, Ill. 60007.

*Effects of Bleeder Cloth Impressions on the Use of Polar Backscatter to Detect Porosity,* 1988 Review of Progress in Quantitative Nondestructive Evaluation, LaJolla, Calif., Jul. 31–Aug. 1988, S. M. Handley, J. G. Miller, Dept. of Physics, Washington University, St. Louis, Mo. 63130; Eric Madaras, NASA Langley Research Center, M/S 231, Hampton, Va. 23665, 1988.

*Porosity Characterization in Fiber–Reinforced Composites By Use of Ultrasonic Backscatter,* Review in Progress in Quantitative NDE v. GB, pp. 1147–1156, (1987), Ronald A. Roberts, Materials and Components Technology Division, Argonne National Laboratory, Argonne, Ill. 60439.

*An Investigation of the Relationship Between Contrast and Azimuthal Angle for Imaging Porosity in Graphite/Epoxy Composites with Ultrasonic Polar Backscatter,* 1988 IEEE Ultrasonic Symposium, Chicago, Ill., Oct. 2–5, 1988, S. M. Handley, J. G. Miller, Dept. of Physics, Washington University, St. Louis, Mo. 63130; Eric Madaras, NASA Langley Research Center, M/S 231, Hampton, Va. 23665, 1988.

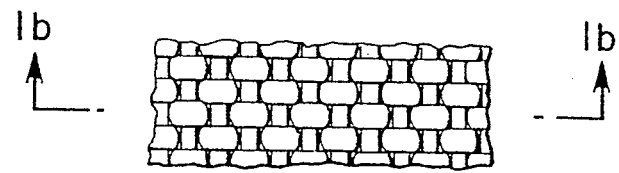
FIG. 1(a)
FIG. 1(b)
FIG. 2
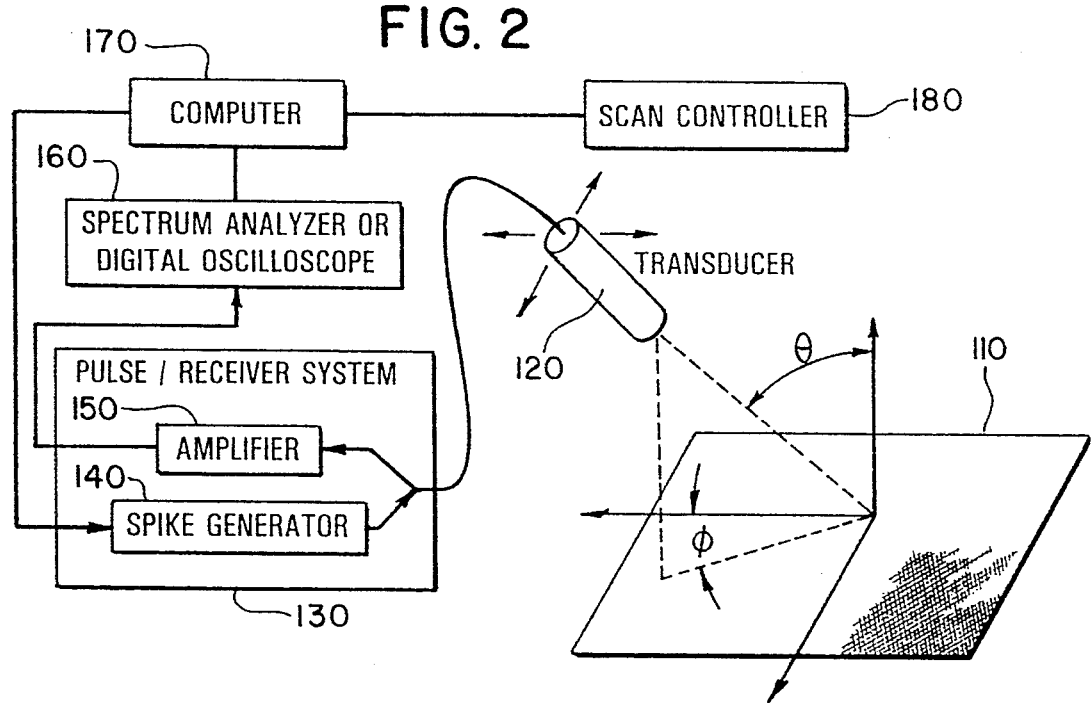
FIG. 4(a)   FIG. 4(b)   FIG. 4(c)
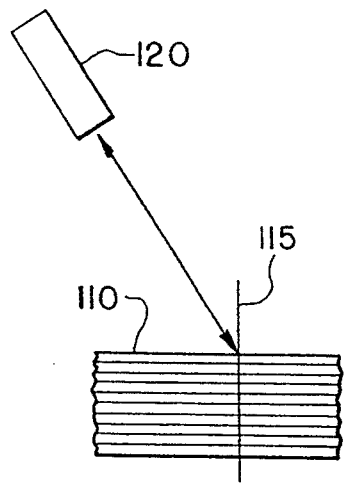 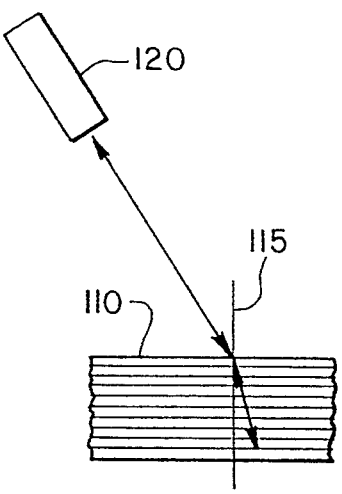 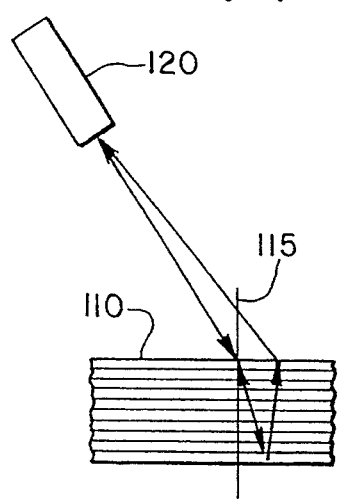

AMPLITUDE DATA FOR DETERMINING FREQUENCY LIMITS

SLOPE DATA FOR DETERMINING FREQUENCY LIMITS

METHOD AND APPARATUS FOR NON-DESTRUCTIVE EVALUATION OF COMPOSITE MATERIALS WITH CLOTH SURFACE IMPRESSIONS

Origin of the Invention

The invention described herein was made by an employee of the U.S. Government and may be manufactured and used by or for the government for governmental purposes without the payment of any royalties thereon or therefor.

BACKGROUND OF THE INVENTION

1. Field of the Invention

The present invention relates generally to non-destructive evaluation of materials by ultrasonic methods, and specifically to the quantitative evaluation of the internal condition of composites by the measurement of Integrated Polar Backscatter from a composite material insonified by an ultrasonic transducer at a non-normal angle of incidence.

2. Description of the Related Art

In a known method for quantitative evaluation of the internal condition of a composite material, the composite is insonified by a single ultrasonic transducer at a non-normal angle of incidence, and a quantity called the Integrated Polar Backscatter is used as a measure of the condition of the composite. The Integrated Polar Backscatter is defined as the total energy of the backscatter signal detected by the transducer over preset frequency ranges, divided by the sum of the frequencies in the preset frequency ranges. The backscatter signals are usually normalized by comparison with the backscatter signal obtained from a reference object, such as a polished stainless steel plate in the same test setup.

When the composite material being tested has a smooth surface, the non-normal angle of incidence of the ultrasonic signal causes the reflected portion of the incident signal to be directed away from the transducer, so it does not contribute to the detected signal. The rest of the incident signal is refracted into the composite, where matrix cracking, porosity, inclusions, or other defects will cause a backscatter signal to be returned to the transducer. Integrated Polar Backscatter accordingly provides an accurate measure of the condition of a composite that has a smooth surface.

In practice, the surface of a composite material is not totally smooth, but has a regular surface texture caused by impressions from a "release cloth", which is a fine mesh cloth impregnated with teflon, used to keep the composite from sticking to the surfaces of the curing press. Such a surface texture causes some of the reflected ultrasonic signal to be directed back to the ultrasonic transducer, so the Integrated Polar Backscatter will have a constant component, independent of the condition of the interior of the composite. This surface backscatter obscures variations in the Integrated Polar Backscatter caused by internal defects, and can make the Integrated Polar Backscatter useless as a quality measure, unless precautions are taken to alleviate the effect of the surface texture.

The obvious remedy for a surface texture is to remove it. Grinding is not a useful method, but a strippable coating of a material with ultrasonic properties matching those of the composite can be applied to the surface of the composite to smooth out the surface texture and effectively eliminate the detrimental effect of the cloth impressions. The application of a coating before the ultrasonic evaluation, and stripping it off afterwards, are time consuming and expensive processes, however. Sometimes quality approval of both the coating material and the application and stripping processes would also be required, which effectively could rule this method out.

An alternate method for reducing the backscattering effect of the cloth impressions involves careful azimuthal alignment of the transducer and the composite material until minimal surface backscatter is obtained. A minimum in the surface backscatter is obtained when the incident signal is parallel to the impressions from either the weft threads or the warp threads in the release cloth. Generally, the surface backscatter has an absolute minimum when the incident signal is in-between the weft threads and warp threads directions. This alignment method can reduce the effect of surface backscatter to tolerable levels in most cases, but the azimuthal alignment is a cumbersome process that is difficult to automate.

SUMMARY OF THE INVENTION

It is an object of the present invention to provide a new method and apparatus for accurate ultrasonic evaluation of the internal condition of a composite material having regular surface impressions from a release cloth through the measurement of Integrated Polar Backscatter.

Another object of the present invention is to provide a method for correctly computing the quantity known as Integrated Polar Backscatter when applied to composite materials with cloth surface impressions.

It is still another object of the present invention to provide a method and apparatus for evaluating the interior of a composite material through the measurement of Integrated Polar Backscatter that can identify and remove signal components caused by surface texture on the composite material.

Even another object of the present invention is to provide a method and apparatus for ultrasonic evaluation of the interior of a composite material by polar backscatter, including elimination of data collected over particular frequency ranges associated with surface texture, It is a still further object of the present invention to provide a new method for evaluation of the interior condition of a composite material by measurement of the quantity known as Integrated Polar Backscatter, which involves automatic detection of effects from surface texture and automatic elimination of such effects from the measured quantity.

In order to achieve the foregoing and other objects, in accordance with the purposes of the present invention as described herein, a method for non-destructive evaluation of composite materials with regular cloth surface impressions comprises the steps of insonifying a series of scan sites on the composite material sequentially with ultrasound at a fixed polar angle larger than zero, recording a power spectrum of the polar backscatter for each scan site, adding the measured backscatter power spectra from several of said scan sites to form a composite power spectrum for polar backscatter, identifying frequency ranges in the composite power spectrum where peaks occur, eliminating the identified frequency ranges from each power spectrum for scan sites of the composite material, and integrating the remaining power spectrum for each scan site to obtain a value for Integrated Polar Backscatter for each scan site substantially free from errors caused by cloth impressions on the surface of the composite.

The theoretical basis for this invention is as follows. In polar backscatter, the sound insonifies the surface at an angle Θ with respect to the surface normal. On a composite surface which has a fabric impression, the surface profile will modulate the angle Θ so that specific locations are nearly perpendicular to the direction of the insonification and reflect the sound back onto the transducer. To model the surface, consider the surface impressions on a panel formed by a fabric in which fill fibers run horizontally and warp fibers run vertically. This pattern indicates a regularly repeated sequence which can be modeled as a series of planar reflectors. This pattern represents a one dimensional reflection grating that will produce interference effects at the measuring transducer. In order to predict the interference effects, the phase relationship of the system of reflectors must be generated. The following equation for the power is derived:

$$|E(f)|^2 = |E_0(f)|^2 M \chi(R,A,a,b) \left( \frac{\sin([N+1]\xi)}{\sin(\xi)} \right)^2 \left( \frac{\sin(4\eta)}{\sin(\eta)} \right)^2 \left( \frac{\sin(2\gamma)}{\sin(\gamma)} \right)^2. \quad \text{eqn. 1}$$

In this equation $|E(f)|^2$ is the reflected signal power, f is the frequency, and $E_0(f)$ is the incident signal amplitude. $X(R,A,a,b)$ is a function that depends on the reflection coefficient R, the total area insonified, A, the reflector width, a, in the x direction and the reflector width, b, in the y direction. M is the number of repeated patterns in the y direction within the beam. N is the number of repeated patterns in the x direction within the beam. $\xi, \eta, Y$ are phase terms.

Eq. 1, in general, will produce narrow peaks in its spectrum that represent the effects of the surface impressions.

BRIEF DESCRIPTION OF THE DRAWINGS

The accompanying drawings illustrate several aspects of the present invention and, together with the descriptions, serve to explain the principles of the invention.

FIGS. 1(a) and 1(b) are an enlarged top view and enlarged sectional view, respectively, showing the surface of a composite material with release cloth imprint;

FIG. 2 is a partly schematic illustration of an apparatus for performing the present invention;

FIGS. 4(a), 4(b) and 4(c) are schematic views illustrating different origins of backscatter signals returned from a composite material;

DETAILED DESCRIPTION OF THE PREFERRED EMBODIMENTS

Figure 3A:
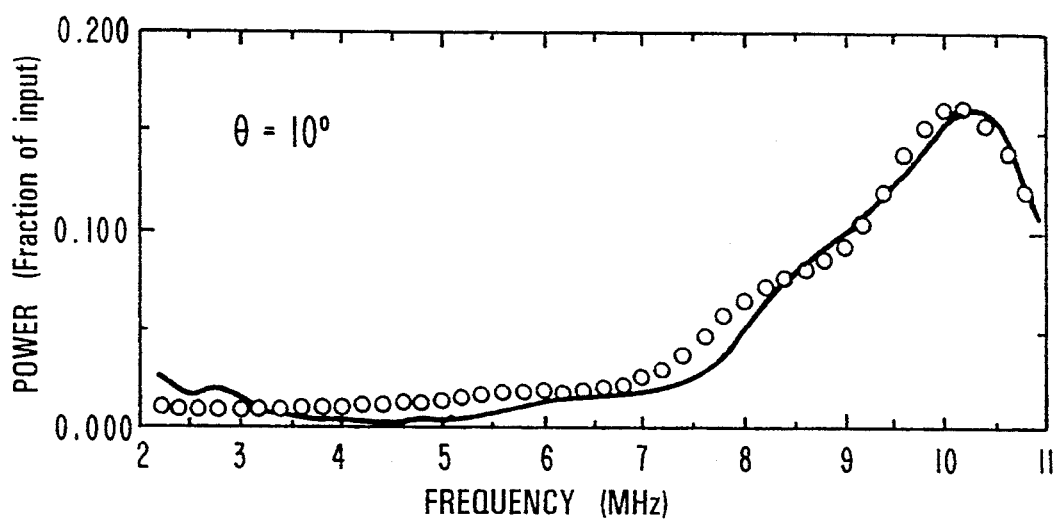
FIGS. 3(a), 3(b) and 3(c) are graphs illustrating frequency spectra for reflected energy at various polar angles Θ.

FIG. 1(a) is an enlarged top view of a composite material, such as a sheet of epoxy/graphite laminate, with a typical surface texture. FIG. 1(b) is an enlarged sectional view taken along line 1b—1b in FIG. 1(a) through the surface of the same material. The depressions visible in FIG. 1(b) are caused by a release cloth used during manufacture to prevent the laminate from sticking to the surfaces of a curing press. The release cloth is stripped off the laminate after the curing is completed.

FIG. 2 is a partly schematic illustration of an apparatus for ultrasonic evaluation of a composite material 110 by measurement of Integrated Polar Backscatter according to the present invention. An ultrasonic transducer 120 is aimed at a composite material 110 at a predetermined polar angle Θ and a predetermined azimuthal angle φ. The transducer 120 is typically a broadband transducer with 5 MHz center frequency, 4 inch focal distance, and 0.5 inch focus width, and it is used in a pulse echo mode. Both the transducer 120 and the composite material 110 are immersed in water or some other suitable coupling medium during measurements.

In order to scan a selected area of the composite sample material 110, the transducer 120 is arranged movable relative to the composite sample material 110 while the polar angle Θ and the azimuthal angle φ are kept constant. After a measurement has been made at one scan site, the relative position is changed by a small increment, e.g. 1/16 inch, and a new measurement is made at the new scan site. This process is repeated until all desired scan sites have been measured. The area insonified by the transducer 120 is typically about ½ inch wide, which is larger than the distance between successive scan sites, so successive scans overlap.

A pulser/receiver system 130 contains a spike generator 140, which periodically generates a spike of approximately −150V to approximately −300V, causing the transducer 120 to emit an ultrasonic wave front aimed at the composite material 110. The pulser/receiver system 130 also contains an amplifier 150 for amplifying backscattered RF signals received by the transducer 120, and a 5μs stepless gate (not shown), which is set to open just before the first reflection is received by the transducer 120. A suitable amplifier 150 is Metrotek MR 106 with a Metrotek MG 701 stepless gate. The output of the amplifier 150 is fed to a spectrum analyzer 160, e.g. a Hewlett Packard 8557 Analog Spectrum Analyzer, which converts the detected time domain signal into a power spectrum and displays it. The signal from the amplifier 150 can alternatively be fed to a device for performing a Fourier transform of the time domain signal, for instance a digital oscilloscope capable of displaying a Fourier transformed frequency plot. In either case, in FIGS. 3(a) through 3(c), a power spectrum of the backscatter signal is displayed with frequency along the abscissa, and the square of the signal strength along the ordinate. The energy in any frequency band is then the area under the graph line in the frequency band.

The reflected signal is typically expressed as a ratio of the amplitude output of the amplifier 150 for the measured backscatter from a composite material as compared with the amplitude of the signal output of the amplifier 150 from a standard material in place of the composite material 110, e.g. a polished metal plate. This normalized signal amplitude is used in all calculations. The normalized amplitude spectrum and power spectrum are commonly displayed on a logarithmic scale and expressed in decibels (dB), but the calculations described below are ordinarily based on linear data values.

The output from the spectrum analyzer or digital oscilloscope 160 is fed to a computer 170, which contains circuitry for controlling the gathering of data, and programs for eliminating signals generated by surface texture on the composite material 110, as will be described in detail below.

FIGS. 4(a) through 4(c) illustrate three types of backscattered signals, which are detected by the transducer 120 and forwarded to the spectrum analyzer 160. Lines 115 are lines normal to the surface of the composite sample material 110.

FIG. 4(a) shows backscatter from the surface of the composite sample material 110. This surface backscatter is negligibly small when the composite sample material 110 has a perfectly smooth top surface, because the signal reflected by the surface in that case will exit to the right of the normal 115 when the polar angle $\Theta$ is larger than zero. If, however, the surface of the composite sample material 110 has a surface texture, e.g. impressions from a release cloth as shown in FIGS. 1(a) and 1(b), the surface texture can cause a significant amount of surface backscatter. This surface backscatter can become so large that it dominates the total backscatter signal. It is the object of the present invention to eliminate its effect on the backscatter measurement.

FIG. 4(b) shows backscatter signal from the interior of the composite sample material 110 by an incident signal refracted into the sample material 110. A flawless composite material will produce a small amount of backscatter of this mode, caused by different sound velocities in the matrix material and the reinforcing fibers of the composite sample material 110. A composite material suffering from delaminations or other defects in the interior of the sample 110 will, however, produce a much larger backscatter signal, and it is this mode of backscatter signal that is desirable for evaluation of the quality of the composite sample material 110.

FIG. 4(c) shows backscatter signal from the far side of the composite sample material 110. This mode of backscatter causes only a small, substantially constant backscatter signal, which does not seriously affect the desired backscatter signal from the mode illustrated in FIG. 4(b).

The test apparatus shown in FIG. 2 has a transducer 120 that emits an ultrasonic beam with a transducer width of $\frac{1}{4}$-inch, so a large number of the small depressions on the surface of the composite material 110 are insonified simultaneously, and the distance between adjacent peaks in the surface texture is comparable to the wavelength of the ultrasonic wave in the coupling medium (water), which is about 0.03 mm at the center frequency of the transducer 120. Under these circumstances, the surface texture on the composite material 110 acts as an ultrasonic grate, so ultrasonic waves will be deflected at different angles to the normal 115 depending on their frequencies. This means that the surface backscatter signal returned to the transducer 120 will contain one or more narrow frequency bands generated by this grating effect.

Figure 3B:
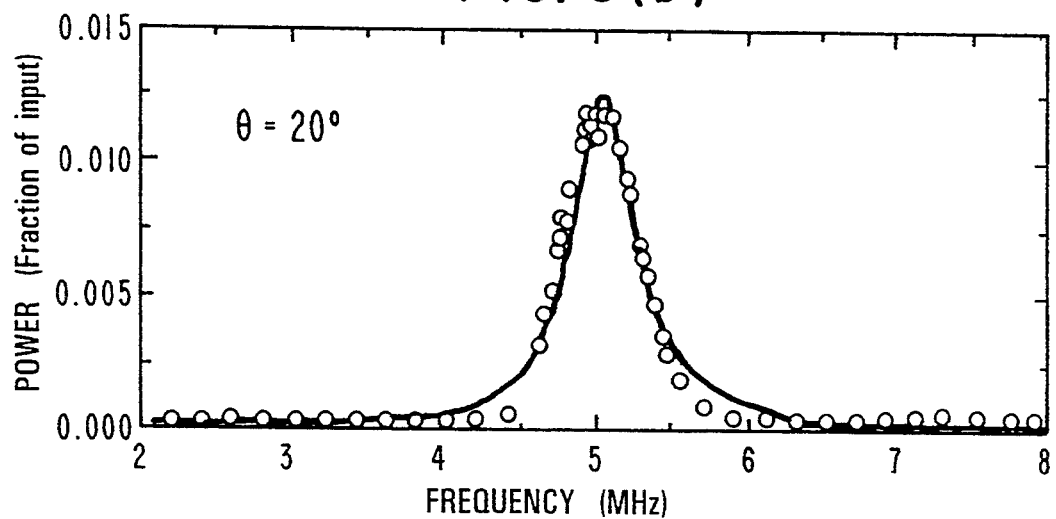
Figure 3C:
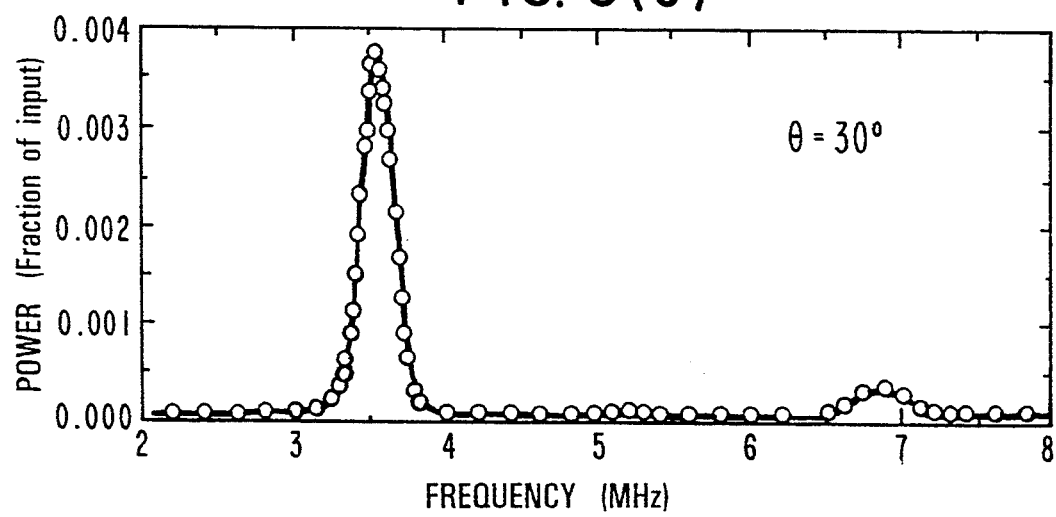

FIGS. 3(a) through 3(c) are graphs showing the power spectra obtained with the apparatus shown in FIG. 2, using samples of laminate with surface texture as illustrated in FIG. 1(b), for different polar angles $\Theta$. The dots represent measured data, while the full solid lines represent data obtained from a theoretical analysis. The agreement between theory and measurement is good. The way the frequencies where peaks appear in FIGS. 3(a) through 3(c) change with the polar angle $\Theta$ is in itself clear indication that the peaks are caused by the grating effect of the surface texture on the composite sample material 110.

The total energy in a frequency range is defined as the area under a power spectrum between the ends of the frequency range. It is evident from FIGS. 3(a) through 3(c) that the areas under the peaks are the major part of the total area under the power spectrum. These parts of the total energy are, however, caused by the surface texture of the composite material, as explained above, so they are independent of the interior quality of the composite material. Accordingly, a much improved measure of the interior quality of a composite material will be obtained if those frequency ranges where peaks occur in the power spectrum are excluded from the calculation of Integrated Polar Backscatter.

The frequency ranges to be excluded according to the present invention are those that exhibit significant peaks caused by the grating effect of the surface texture. These excluded frequency ranges can easily be determined for a particular composite material at a particular polar angle $\Theta$ and azimuthal angle $\phi$, either manually or by a computer algorithm, as will be described below. Correct values for Integrated Polar Backscatter, independent of artifacts caused by surface texture, can then be obtained for later scan sites on the composite material 110 by integrating the power only over the frequency ranges not excluded.

Figure 5:
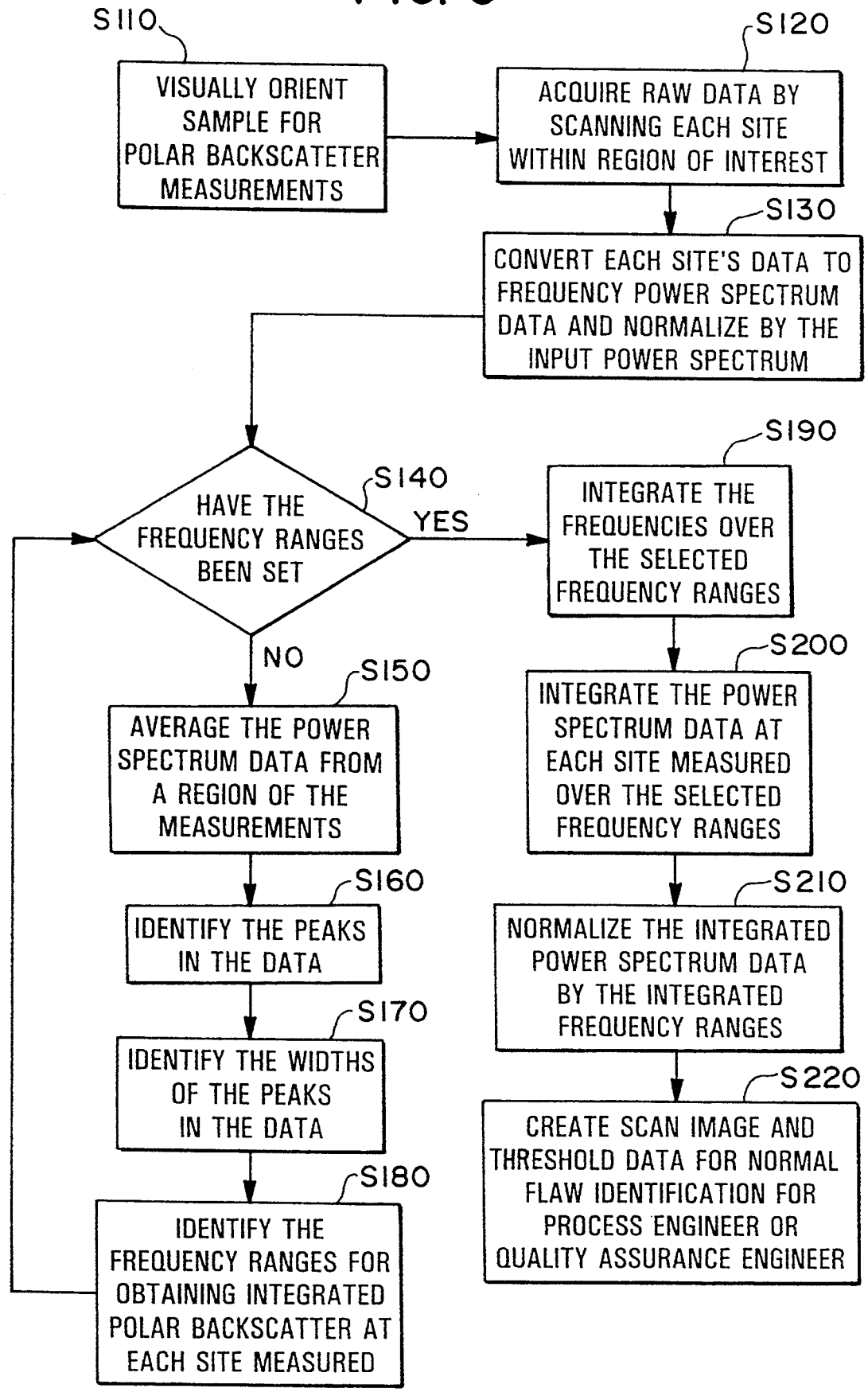
FIG. 5 is a flow chart for a method of computing Integrated Polar Backscatter with surface effects eliminated.

FIG. 5 is a flow chart of a method for computer processing of the data received from the transducer 120 via the spectrum analyzer 160.

In step S110, the azimuthal angle $\phi$ of the composite sample material 110 is visually oriented relative to the transducer 120. The composite sample material 110 should in step S110 preferably be aligned so azimuth $\phi = 0$ corresponds to the direction of impressions from weft threads in the surface of the composite material 110, but exact alignment of the sample material is not necessary, as long as the azimuthal angle $\phi$ remains constant during the entire test sequence.

In step S120, the surface of the composite sample material 110 is scanned by the transducer 120 over an area of interest to obtain raw data.

In step S130, the raw time domain data from step S120 is next transformed into the frequency domain using a spectrum analyzer or digital Fourier transform methods, and the power spectrum is calculated. This power spectrum is normalized (calibrated) by a reference signal earlier obtained from a polished stainless steel plate used as a target instead of the composite sample material 110 to represent the power that is transmitted into the composite sample material 110. The recording of the raw time domain data and conversion to a power spectrum in the frequency domain can be made by modern digital oscilloscopes, which have internal numerical signal processing computers that are optimized for fast and efficient Fourier transforms and can internally store and subtract signals. A spectrum analyzer could instead be used to give the power spectrum directly. A spectrum analyzer often has very high fidelity, but may be slower. Alternatively, the conversion by digital Fourier transform methods could also be performed within the computer 170.

In step S140, it is determined if the frequency ranges affected by surface backscatter have been set. If they have not been set, which is the case when a new sample 110 is being analyzed, step S140 continues to step S150. If the frequency ranges have been set, step S140 continues to step S190.

In step S150, all of the data, or data from a few selected scan sites, are next averaged to form a composite power spectrum, which will be used to determine which frequency ranges are affected by surface backscatter. Scans over a small region can often be used to identify the frequency ranges of interest for the whole data set.

The processing after step S150 continues in step S160, where significant peaks are identified by using a maximum/minimum identification algorithm. The significant peaks can be selected by first identifying the maximum and minimum power amplitudes in the entire frequency range, and calculating the maximum minus minimum value. Significant individual peaks would then typically be defined as peaks with a peak maximum minus peak minimum value that is greater than 20% of the overall maximum minus minimum value, or in mathematical terms:

(peak max-peak min)/(max-min) > 0.2.

Maximum/minimum identification algorithms could scan the data set in a straight forward manner testing for peaks and minima, or alternatively, by numerically differentiating the power spectrum (in the linear domain) with respect to the frequency, and testing those results for positive to negative transitions, which will identify frequencies where the power spectrum has undergone a maximum. It may be necessary to smooth the data, e.g. by means of a low pass filter, in order to remove signal noise before the differentiation.

Figure 6A:
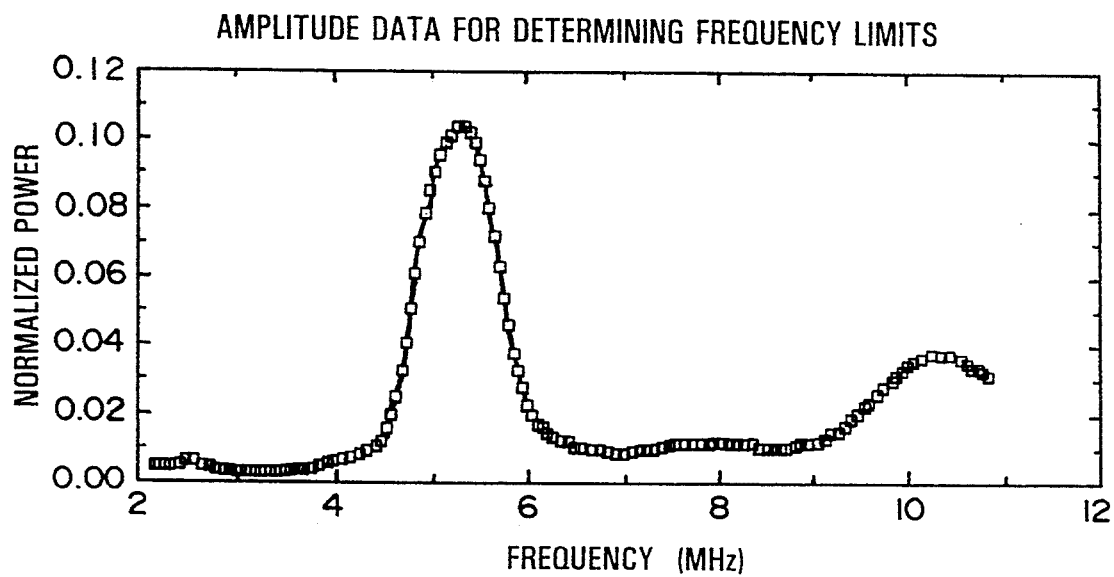
FIGS. 6(a), 6(b), 6(c) and 6(d) are graphs illustrating different steps in the method for eliminating frequency ranges containing the surface backscatter signal.

FIG. 6(a) is a plot of smoothed data from a composite sample material 110 of normalized power plotted with respect to frequency. The surface texture on the composite sample material 110 introduces the signal artifacts appearing as peaks in FIG. 6(a). It is easily calculated that a minimum power of 0.00298 occurs at a frequency of 3.1 MHz, and a maximum power of 0.10584 occurs at a major peak at a frequency of 5.4 MHz. The max-min is therefore 0.10286. At a 20% cutoff, there is only one other significant peak, located at a frequency of 10.3 MHz.

Figure 6B:
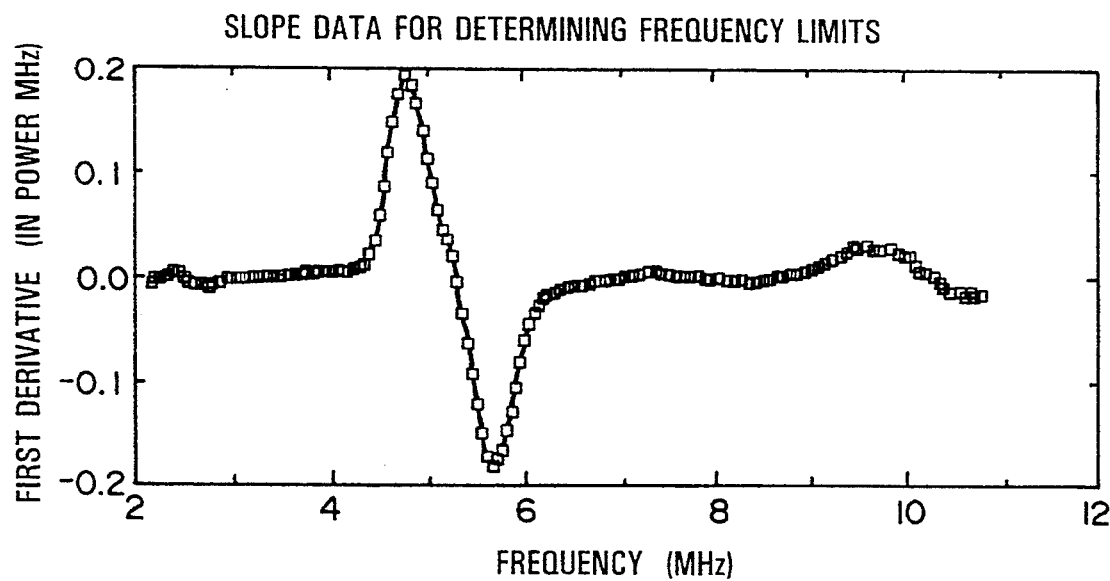

FIG. 6(b) is a plot of the first derivative of the data of FIG. 6(a). The two significant peaks can be identified by their positive to negative transitions points at frequencies 5.4 MHz and 10.3 MHz in the first derivative data.

In step 170 of FIG. 5, the widths of the major peaks are determined. This is easiest to do by testing for maxima and minima in the first derivative with respect to frequency. Such maxima and minima in the first derivative represent the frequency locations of the "half widths" of the peaks. From FIG. 6(b), the locations of the maximum and minimum positions identify the steepest slopes as well as the frequencies where they occur. In the case shown in FIG. 6(b), the locations are first peak left half width at a frequency of 4.8 MHz, first peak right half width at a frequency of 5.65 MHz, second peak left half width at a frequency of 9.6 MHz and second peak right half width at a frequency of 10.75 MHz.

Figure 6C:
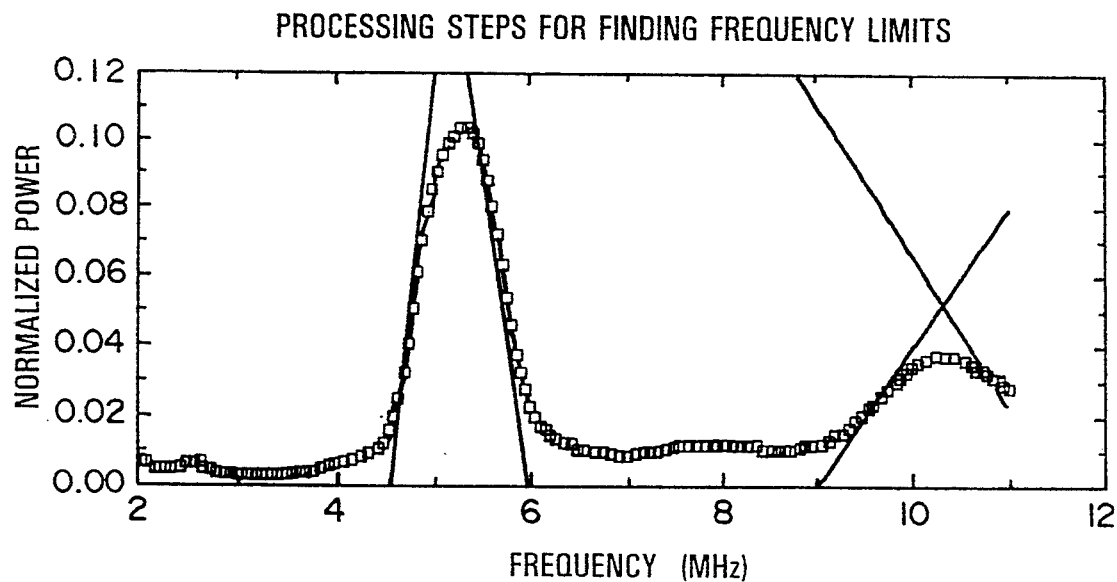

In step S180 of FIG. 5, the frequency ranges to be used in the calculation of Integrated Polar Backscatter for each scan site are determined. Once the half width locations are found as explained above with reference to step S170, the values for the maxima and minima in the first derivative data give the slopes of the peaks at the half width locations. The straight lines shown in FIG. 6(c) are calculated by step S180. They are tangents to the slopes of the peaks at the frequencies calculated under step S170, and their slopes are defined by the values of the maxima and minima in the first derivative with respect to frequency at those frequencies, as illustrated in FIG. 6(b). The resulting intercepts with the abscissa are frequencies of 4.6 MHz, 6.05 MHz and 9.05 MHz. Each frequency range between a pair of intersections spanning a peak represents a frequency range tainted by surface backscatter from surface texture, and all such frequency ranges should be eliminated from the calculation of the Integrated Polar Backscatter. Only the remaining frequency ranges are identified in step S180 of FIG. 5, and only these frequency ranges will be used in calculating the Integrated Polar Backscatter for each scan site.

Figure 6D:
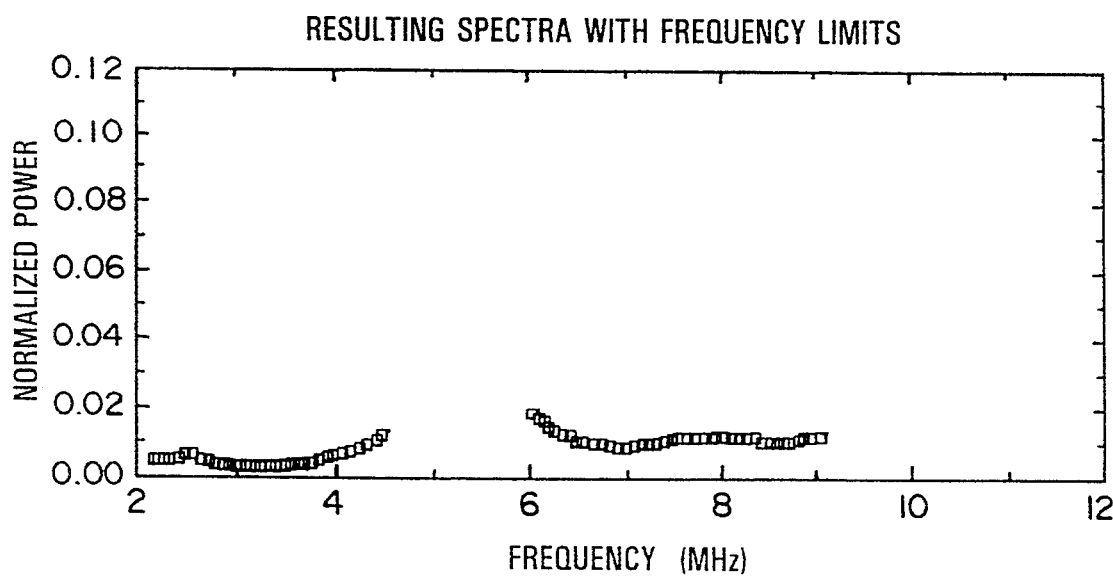

FIG. 6(d) is a graph showing a normalized power spectrum for the resulting usable frequency ranges for analyzing the composite sample material 110. The other frequency ranges have been excluded because these were determined by the above procedure as containing erroneous data due to surface texture. Thus, by integration over only the ranges indicated in FIG. 6(d), the effect of surface texture is eliminated from the calculated Integrated Polar Backscatter.

After the frequency ranges have been set by steps S150 through S180, step S140 proceeds to the procedure for integration and detection of flaws in steps S190 through S220.

In step S190 of FIG. 5, the usable frequency ranges defined in step S180 are summed, thereby defining the denominator in later calculations of Integrated Polar Backscatter.

In step S200 of FIG. 5, the power spectrum for each scan element previously recorded under step S120, or recorded separately later on, is first derivative data give the slopes of the peaks at the half width locations. The straight lines shown in FIG. 6(c) are calculated by step S180. They are tangents to the slopes of the peaks at the frequencies calculated under step S170, and their slopes are defined by the values of the maxima and minima in the first derivative with respect to frequency at those frequencies, as illustrated in FIG. 6(b). The resulting intercepts with the abscissa are frequencies of 4.6 MHz, 6.05 MHz and 9.05 MHz. Each frequency range between a pair of intersections spanning a peak represents a frequency range tainted by surface backscatter from surface texture, and all such frequency ranges should be eliminated from the calculation of the Integrated Polar Backscatter. Only the remaining frequency ranges are identified in step S180 of FIG. 5, and only these frequency ranges will be used in calculating the Integrated Polar Backscatter for each scan site.

FIG. 6(d) is a graph showing a normalized power spectrum for the resulting usable frequency ranges for analyzing the composite sample material 110. The other frequency ranges have been excluded because these were determined by the above procedure as containing erroneous data due to surface texture. Thus, by integration over only the ranges indicated in FIG. 6(d), the effect of surface texture is eliminated from the calculated Integrated Polar Backscatter.

After the frequency ranges have been set by steps S150 through S180, step S140 proceeds to the procedure for integration and detection of flaws in steps S190 through S220.

In step S190 of FIG. 5, the usable frequency ranges defined in step S180 are summed, thereby defining the denominator in later calculations of Integrated Polar Backscatter.

In step S200 of FIG. 5, the power spectrum for each scan element previously recorded under step S130, or recorded separately later on, is integrated over the usable frequency ranges determined in Step S180 to obtain the total energy.

In step S210 of FIG. 5, the total energy for each scan site calculated in step S200 is divided by the summed frequencies calculated in step S190, to produce an Integrated Polar Backscatter value for each scan site by normalization.

Finally, in step S220 of FIG. 5, a visual map is generated, with each scanned site being identified by a small square or rectangle ("pixel"). The color or gray level of the pixel can be used to provide an image representing the amplitude of the integrated polar backscatter. This visual map can also be thresholded to produce a binary image representing good versus flawed material.

The present invention offers several important advantages over the prior art. A major advantage is that it requires no sample preparation for implementation. The present invention further requires only that digital data be obtained for processing in the frequency domain, and this is already becoming the standard method of ultrasonic data acquisition in field installations. The method according to the invention can also be performed using software with the data after the scan has been finished, so it has little impact on the initial data scan time for the sample.

Many variations of the method and apparatus described herein are possible within the scope of the invention. For instance, frequency ranges where the recorded power is tainted by surface backscatter can be determined by fitting measured data to formulas based on grating theory, instead of by the empirical determination described above.

The composite power spectrum used to determine the tainted frequency ranges can be based on data from all the measured scan sites when a complete set of data is recorded, and the Integrated Polar Backscatter can be calculated from the recorded data base. Alternatively, data from only a few selected scan sites can first be used to determine the excluded frequency ranges, and a full set of scans can later be taken, with each pixel immediately being identified as either good or bad as the scan is progressing.

It would also be possible to do the summation for the composite power spectrum in the logarithmic domain, instead of in the linear domain. Because of the signal compression that the logarithmic values represent, this would improve the signal to noise ratio. It would, however, be necessary to convert the composite power data to linear values before further calculations to determine the frequency ranges to be excluded.

Numerous further modifications and adaptations of the present invention will become apparent to those skilled in the art. Thus, the following claims are intended to cover all such modifications and adaptations which fall within the true spirit and scope of the present invention.

What is claimed is:

1. A method for non-destructive evaluation of composite materials with regular surface impressions, comprising the steps of:
   (a) insonifying at least one scan site on a composite material with ultrasound at a fixed polar angle larger than zero and a fixed azimuthal angle;
   (b) detecting a backscattered ultrasound return signal from the composite material;
   (c) amplifying the return signal;
   (d) transforming the amplified return signal into a polar backscatter power spectrum for each scan site;
   (e) summing the polar backscatter power spectra from each scan site to form a composite power spectrum for polar backscatter;
   (f) identifying frequency ranges in said composite power spectrum where significant peaks occur;
   (g) eliminating said identified frequency ranges from each polar backscatter power spectrum for each scan site of the composite material giving a corrected polar backscatter power spectrum for each scan site;
   (h) integrating the corrected polar backscatter power spectrum for each scan site to obtain a value for Integrated Polar Backscatter for each scan site substantially free from artifacts caused by regular impressions on the surface of the composite material; and
   (i) displaying a map comprised of pixels, wherein each pixel indicates the value of the substantially artifact-free Integrated Polar Backscatter at a corresponding scan site.

2. A method for non-destructive evaluation of composite materials with regular surface impressions according to claim 1, wherein step (f) further comprises the steps of:
   smoothing the power spectrum;
   plotting the first derivative of said smoothed power spectrum with respect to frequency;
   determining the frequencies where said first derivative has zero values;
   determining the frequencies where said first derivative has peaks and valleys adjacent to said frequencies corresponding to zero values;
   determining the amplitude values for said peaks and valleys;
   plotting straight lines intersecting said composite power spectrum at each of said frequencies corresponding to peaks and valleys in the first derivative plot and having slopes equal to said amplitudes values of corresponding said peaks and valleys;
   determining where said straight lines intersect the frequency axis of said composite spectrum; and
   defining a peak area as the frequency range between a pair of said straight line said pair being chosen such that between them lies a frequency range where said first derivative has a zero value.

3. The method for non-destructive evaluation of composite materials with regular surface impressions according to claim 1, wherein step (f) further comprises the steps of:
   determining the total maximum and the total minimum amplitude in the composite power spectrum, and calculating the difference therebetween;
   determining the differences between peaks and minima for individual peaks in the composite power spectrum;

dividing the difference between peak and minimum for each individual peak by the difference between the total maximum and total minimum and recording the quotient for each division; and designating as significant those peaks having said quotient exceeding a predetermined threshold value.

4. An apparatus for non-destructive evaluation of the interior of composite materials having regular surface impressions, comprising:

(a) a broadband ultrasonic transducer in pulse echo mode focused at a test site on the surface of a composite material at a non-normal angle of incidence, and means for causing a wave front to be emitted from said transducer;

(b) amplifying means for amplifying time domain signals from said transducer during predetermined gating intervals;

(c) converting means for converting the amplified time domain signals to a power spectrum in the frequency domain;

(d) a processing means for manipulating the power spectrum, the processing means being capable of detecting peaks in the power spectrum, identifying frequency ranges associated with the peaks, summing frequencies excluding the identified frequency ranges to obtain a net sum of frequencies, integrating the power spectrum over frequencies excluding the identified frequency ranges to obtain a net value for total energy, and calculating the quotient of the net value for total energy and the net sum of frequencies to obtain a quantity known as Integrated Polar Backscatter and comparing the Integrated Polar Backscatter with a reference value to determine if the Integrated Polar Backscatter represents a defective composite material.

5. The apparatus for non-destructive evaluation of the interior of composite materials with regular surface impressions according to claim 4, wherein said converting means is an analog spectrum analyzer.

6. The apparatus for non-destructive evaluation of the interior of composite materials with regular surface impressions according to claim 4, wherein said converting means is a digital computer programmed to perform Fourier transforms.

7. The apparatus for non-destructive evaluation of the interior of composite materials with regular surface impressions according to claim 4, wherein a digital computer is programmed to serve as the processing means.

* * * * *

UNITED STATES PATENT AND TRADEMARK OFFICE
CERTIFICATE OF CORRECTION

PATENT NO. : 5,390,544
DATED : February 21, 1995
INVENTOR(S) : Eric I. Madaras

It is certified that error appears in the above-indentified patent and that said Letters Patent is hereby corrected as shown below:

On the title page, under item [19] and item [75], change "Madras" to --Madaras--.

Signed and Sealed this

Second Day of May, 1995

*Attest:*

BRUCE LEHMAN

*Attesting Officer*       *Commissioner of Patents and Trademarks*